US009373953B2

(12) United States Patent
Kimura (10) Patent No.: US 9,373,953 B2
(45) Date of Patent: Jun. 21, 2016

(54) BATTERY PROTECTING CIRCUIT, BATTERY PROTECTING DEVICE, AND BATTERY PACK

(71) Applicant: Daisuke Kimura, Tokyo (JP)

(72) Inventor: Daisuke Kimura, Tokyo (JP)

(73) Assignee: MITSUMI ELECTRIC CO., LTD., Tokyo (JP)

( * ) Notice: Subject to any disclaimer, the term of this patent is extended or adjusted under 35 U.S.C. 154(b) by 821 days.

(21) Appl. No.: 13/727,912

(22) Filed: Dec. 27, 2012

(65) Prior Publication Data

US 2013/0202918 A1 Aug. 8, 2013

(30) Foreign Application Priority Data

Feb. 2, 2012 (JP) ................................ 2012-021161

(51) Int. Cl.
*H02J 7/00* (2006.01)
*H01M 10/00* (2006.01)
(Continued)

(52) U.S. Cl.
CPC *H02H 3/207* (2013.01); *H02J 7/00* (2013.01); *H02J 7/0016* (2013.01); *H02J 7/0031* (2013.01); *G01N 27/416* (2013.01); *G08B 21/00* (2013.01); *H01M 10/425* (2013.01); *H02J 2007/004* (2013.01); *H02J 2007/0037* (2013.01)

(58) Field of Classification Search
CPC ......... H02J 7/00; H02J 7/0016; H02J 7/0031; H02J 2007/0037; H02J 2007/004; H01M 10/425; H02H 3/207; G01N 27/416; G08B 21/00
USPC .............. 320/134, 136; 324/434; 340/636.17, 340/636.19
See application file for complete search history.

(56) References Cited

U.S. PATENT DOCUMENTS

2004/0036446 A1 2/2004 Iwashima
2005/0068008 A1 3/2005 Zhang
(Continued)

FOREIGN PATENT DOCUMENTS

JP 08-308115 11/1996
JP 2000-014020 1/2000
(Continued)

OTHER PUBLICATIONS

Hiromitsu et al., Machine English Translation of Japanese Patent Document No. JP 2000-014020 A, Published Jan. 14, 2000, machine translated on Nov. 29, 2015 via www.j-platpat.inpit.go.jp.*
(Continued)

*Primary Examiner* — Phallaka Kik
(74) *Attorney, Agent, or Firm* — IPUSA, PLLC (57) ABSTRACT

A disclosed battery protecting circuit for protecting a secondary battery including at least first and second cells connected in series includes a first terminal connected on a high potential side of the first cell; a second terminal connected on a low potential side of the first cell and a high potential side of the second cell; a third terminal connected on a low potential side of the second cell; a charge abnormality detecting circuit detecting abnormality of the charged state of the secondary battery; a shifting circuit shifting electric potential of the second terminal on a side of the first terminal or a third terminal when a disconnection occurs between the secondary battery and the second terminal; a disconnection detecting circuit detecting the disconnection based on the electric potential of the second terminal; and a latching circuit retaining a result detected by the disconnection detecting circuit.

8 Claims, 3 Drawing Sheets

(51) Int. Cl.
*H02H 3/00* (2006.01)
*G01N 27/416* (2006.01)
*G08B 21/00* (2006.01)
*H02H 3/20* (2006.01)
*H01M 10/42* (2006.01)

(56) References Cited

U.S. PATENT DOCUMENTS

| | | |
|---|---|---|
| 2006/0267557 A1 | 11/2006 | Nakano et al. |
| 2007/0096695 A1* | 5/2007 | Kimura .................. H02J 7/0031 320/134 |
| 2009/0051324 A1* | 2/2009 | Nakatsuji ............ H01M 10/441 320/134 |
| 2011/0050172 A1 | 3/2011 | Sano et al. |
| 2011/0089906 A1* | 4/2011 | Sakurai ................. H02J 7/0031 320/134 |
| 2011/0101918 A1* | 5/2011 | Tsukamoto .......... G01R 31/362 320/118 |

FOREIGN PATENT DOCUMENTS

| | | |
|---|---|---|
| JP | 2004-104989 | 4/2004 |
| JP | 2005-094907 | 4/2005 |
| JP | 2006-340450 | 12/2006 |
| JP | 2007-124867 | 5/2007 |
| JP | 2011-072177 | 4/2011 |

OTHER PUBLICATIONS

Japanese Office Action mailed Jul. 28, 2015 for Japanese Patent Application No. 2012-021161.

* cited by examiner

BATTERY PROTECTING CIRCUIT, BATTERY PROTECTING DEVICE, AND BATTERY PACK

CROSS-REFERENCE TO RELATED APPLICATIONS

This patent application is based upon and claims the benefit of priority of Japanese Patent Application No. 2012-021161 filed on Feb. 2, 2012 the entire contents of which are incorporated herein by reference.

BACKGROUND OF THE INVENTION

1. Field of the Invention

The present invention generally relates to a battery protecting circuit which protects plural secondary batteries connected in series, and a battery protecting device. Further, the present invention relates to a battery pack having the battery protecting device.

2. Description of the Related Art

An example of a lithium-ion secondary battery is formed by a multistage stack of plural cells. However, when a line or the like between the lithium-ion secondary battery and a monitoring terminal for monitoring the cell voltages of the cells is broken and disconnected, the corresponding cell voltage cannot be accurately monitored. Therefore, if the charged state of the cell is an abnormal state such as overcharge or overdischarge, the abnormal state may not be detected. The battery protecting circuit may have a disconnection detecting function in order to avoid such an abnormal state. Patent Document 1 discloses a method of detecting disconnection by pulling up or down the monitoring terminal using a constant current circuit to shift the electric potential of the monitoring terminal when the disconnection of the monitoring terminal occurs.

[Patent Document 1] Japanese Laid-open Patent Publication No. Hei 8-308115

SUMMARY OF THE INVENTION

Accordingly, embodiments of the present invention may provide a novel and useful battery protecting circuit, a battery protecting device, and a battery pack solving one or more of the problems discussed above.

More specifically, the embodiments of the present invention may provide a battery protecting circuit for protecting a secondary battery including at least a first cell and a second cell, which are connected in series, the battery protecting circuit including a first terminal connected on a high potential side of the first cell; a second terminal connected on a low potential side of the first cell and a high potential side of the second cell; a third terminal connected on a low potential side of the second cell; a charge abnormality detecting circuit which detects abnormality of the charged state of the secondary battery; a shifting circuit for shifting electric potential of the second terminal on a side of the first terminal or on a side of a third terminal when a disconnection occurs between the secondary battery and the second terminal; a disconnection detecting circuit for detecting the disconnection based on the electric potential of the second terminal; and a latching circuit for retaining a result detected by the disconnection detecting circuit.

Additional objects and advantages of the embodiments are set forth in part in the description which follows, and in part will become obvious from the description, or may be learned by practice of the invention. The objects and advantages of the invention will be realized and attained by means of the elements and combinations particularly pointed out in the appended claims. It is to be understood that both the foregoing general description and the following detailed description are exemplary and explanatory and are not restrictive of the invention as claimed.

DETAILED DESCRIPTION OF THE PREFERRED EMBODIMENTS

However, even if the line or the like between the secondary battery and the monitoring terminal is disconnected, the electric potential of the monitoring terminal may be unstable as not being fixed to the value of a shifted electric potential. Such an unstable state may be caused by unstable disconnection such as partial disconnection or connection failure, or an operation of another circuit connected to the monitoring terminal. In such a case, there may be a case where the operation which should be performed in detecting the disconnection is not properly performed.

A description is given below, with reference to the FIG. 1 through FIG. 3 of embodiments of the present invention.

Reference symbols typically designate as follows:
1: charge controlling transistor;
2: discharge controlling transistor;
5, 6: load connecting terminal;
7: charge and discharge controlling unit;
8a, 9b: power source route;
10, 10A, 10B: battery protecting IC;
11-19: outer terminal;
21-25: cell balancing circuit;
30: secondary battery;
31-35: cell;
41-46: cell connecting terminal;
51-56: connecting wire;
61-65: cell balancing IC;
80: protecting module;
90: outer load;
100: battery pack;
101-105: intermediate potential fixing circuit;
110: charge abnormality detecting circuit;
111-115: detector;
120: disconnection detecting circuit;
121-124: comparator;
125: OR circuit;
130: latching function selecting circuit;
140: disconnection detecting function selecting circuit;
155: latching circuit;
158: controlling circuit;
T: transistor; and
R: resistor.

Figure 1:
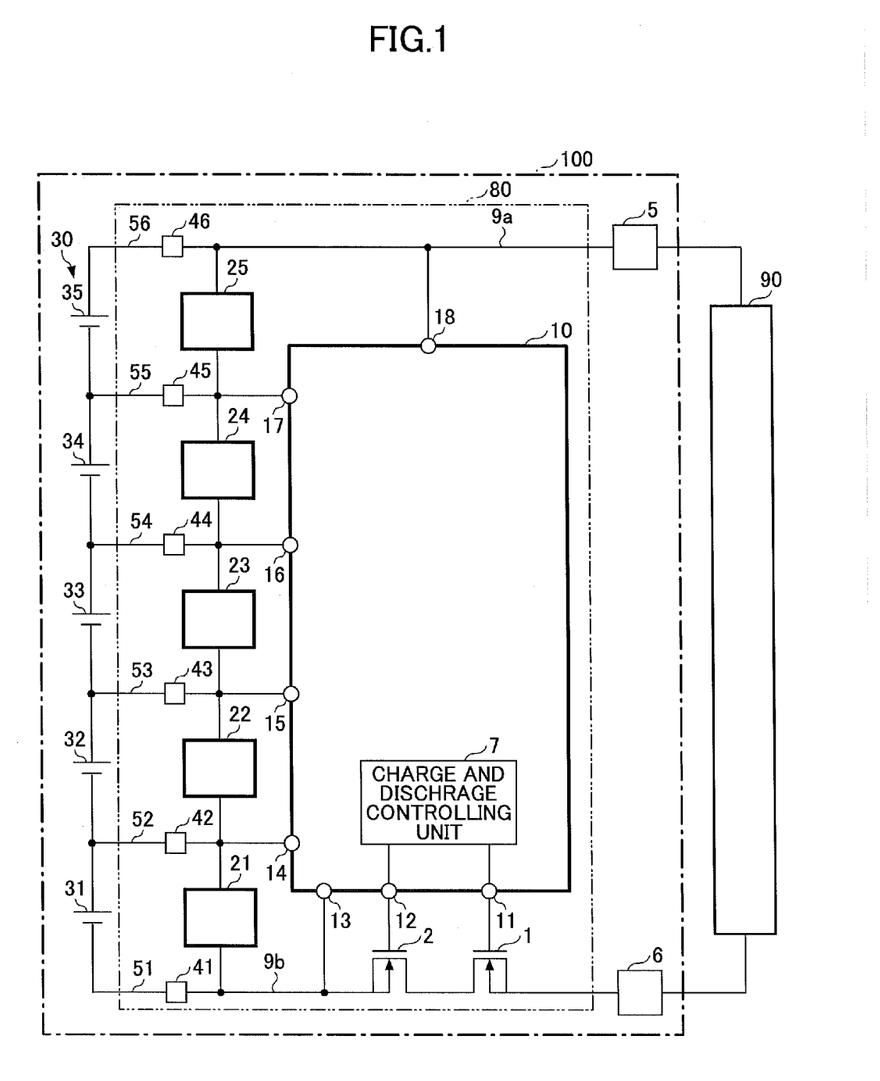
FIG. 1 illustrates an exemplary structure of a battery pack.

FIG. 1 illustrates an exemplary circuit of a battery pack 100 of an embodiment. The battery pack 100 has a secondary battery 30 which can supply electric power to an outer load 90 connected to load connecting terminals 5 and 6, and a protecting module 80 which protects the secondary battery 30. The secondary battery 30 and the protecting module 80 are built into the battery pack 100. The battery pack 100 may be built into the outer load 90 or attached to the outside of the outer load 90. Specifically, the outer load 90 is an electric power tool, an electrical power assisted bicycle, an electric motorcycle, or the like.

The secondary battery 30 can be charged by a charger (not illustrated) which is connected to the load connecting terminals 5 and 6. An exemplary secondary battery 30 is a lithium-ion battery or the like. The secondary battery 30 is formed of plural cells which are connected in series. Referring to FIG. 1, five cells 31 to 35 are exemplified.

The positive terminal of the secondary battery 30 is connected to the positive terminal of the cell 35 positioned at the highest electric potential among the cells 31 to 35. The negative terminal of the secondary battery 30 is connected to the negative terminal of the cell 31 positioned at the lowest electric potential among the cells 31 to 35. The positive terminal of a cell exists on the side of higher electric potential in the cell. The negative terminal of a cell exists on the side of lower electric potential in the cell.

The protecting module 80 functions as a battery protecting device including the load connecting terminal 5, the load connecting terminal 6, and cell connecting terminals 41 to 46. The cell connecting terminal 46 is connected to the load connecting terminal 5 via an electric power line 9a. The cell connecting terminal 41 is connected to the load connecting terminal 6 via an electric power line 9b.

The cell connecting terminal 41 is connected to the negative terminal of the secondary battery and the negative terminal of the cell 31 via a connecting wire 51. The cell connecting terminal 42 is connected to the positive terminal of the cell 31 and the negative terminal of the cell 32 via a connecting wire 52. The cell connecting terminal 43 is connected to the positive terminal of the cell 32 and the negative terminal of the cell 33 via a connecting wire 53. The cell connecting terminal 44 is connected to the positive terminal of the cell 33 and the negative terminal of the cell 34 via a connecting wire 54. The cell connecting terminal 45 is connected to the positive terminal of the cell 34 and the negative terminal of the cell 35 via a connecting wire 55. The cell connecting terminal 46 is connected to the positive terminal of the secondary battery 30 and the positive terminal of the cell 35 via a connecting wire 56.

The protecting module 80 includes plural cell balancing circuits 21 to 25. Cell balancing circuits 21 to 25 are correspondingly connected to the cells 31 to 35 in parallel. The cell balancing circuits 21 to 25 are equalization circuits for reducing unevenness of the cell voltages of the cells 31 to 35. The cell balancing circuit 21 is connected to the cell 31 in parallel via the connecting wires 51 and 52. The cell balancing circuit 22 is connected to the cell 32 in parallel via the connecting wires 52 and 53. The cell balancing circuit 23 is connected to the cell 33 in parallel via the connecting wires 53 and 54. The cell balancing circuit 24 is connected to the cell 34 in parallel via the connecting wires 54 and 55. The cell balancing circuit 25 is connected to the cell 35 in parallel via the connecting wires 55 and 56.

The cell balancing circuit 21 causes the cell 31 to start discharging if the cell voltage of the cell 31 becomes a predetermined threshold for starting discharging or greater. The cell balancing circuit 21 causes the cell 31 to stop discharging if the cell voltage of the cell 31 becomes a predetermined threshold for starting discharging or smaller. A threshold for stopping discharging is set to be equal to or less than the threshold for starting discharging. In a manner similar to the cell balancing circuit 21, as for the cell balancing circuits 22 to 25, discharging of the cell is controlled depending on the cell voltage of the corresponding cell. By equalizing the thresholds for starting discharging and the thresholds for stopping discharging, respectively set for the cell balancing circuits 21 to 25, the cell voltages of the cells 31 to 35 are mutually equalized. Said differently, balances of the cell voltages between the cells 31 to 35 can be maintained.

The protecting module 80 includes transistors 1 and 2. The transistor 1 is a charging route shutoff unit for shutting off a charging route for the secondary battery 30. The transistor 2 is a discharging route shutoff unit for shutting off a discharging route for the secondary battery 30. Referring to FIG. 1, the transistor 1 shuts off the electric power line 9b through which a charging current flows. The transistor 2 shuts off the electric power line 9b through which a discharging current flows. The transistors 1 and 2 are switching elements for switching over conduction and shutdown of the electric power line 9b. The transistors 1 and 2 are arranged in series in the electric power line 9b.

For example, the transistors 1 and 2 are MOSFETs. The transistor 1 is inserted into the electric power line 9b so that the forward direction of a parasitic diode of the transistor 1 becomes the discharging direction of the secondary battery 30. The transistor 2 is inserted into the electric power line 9b so that the forward direction of a parasitic diode of the transistor 2 becomes the charging direction of the secondary battery 30. The transistors 1 and 2 may be another type of semiconductor element such as an IGBT or a bipolar transistor. A diode may be added between the drain and the source (or the collector and the emitter) of each of the transistors 1 and 2.

The protecting module 80 includes a battery protecting IC (hereinafter, "a protecting IC") 10. The protecting IC 10 is an integrated circuit for protecting the cells 31 to 35.

The protecting module 80 outputs a high level signal for turning on the transistor 1 or a low level signal for turning off the transistor 1 from a terminal 11 of the protecting IC 10. The protecting IC 10 allows an electric current to flow through the electric power line 9b in the charging direction for charging the secondary battery 30 by turning on the transistor 1. The protecting IC 10 prevents the electric current from flowing through the electric power line 9b in the charging direction for charging the secondary battery 30 by turning off the transistor 1.

The protecting module 80 outputs a high level signal for turning on the transistor 2 or a low level signal for turning off the transistor 2 from a terminal 12 of the protecting IC 10. The protecting IC 10 allows an electric current to flow through the electric power line 9b in the discharging direction for discharging the secondary battery 30 by turning on the transistor 2. The protecting IC 10 prevents the electric current from flowing through the electric power line 9b in the discharging direction for discharging the secondary battery 30 by turning off the transistor 2.

The protecting IC 10 includes a charge and discharge controlling unit 7. The charge and discharge controlling unit 7 acquires a detected voltage value between terminals 13 and 14 as a detected cell voltage value of the cell 31. The charge and discharge controlling unit 7 acquires a detected voltage value between the terminal 14 and a terminal 15 as a detected cell voltage value of the cell 32. The charge and discharge controlling unit 7 acquires a detected voltage value between the terminal 15 and a terminal 16 as a detected cell voltage value of the cell 33. The charge and discharge controlling unit 7 acquires a detected voltage value between the terminal 16 and a terminal 17 as a detected cell voltage value of the cell 34. The charge and discharge controlling unit 7 acquires a detected voltage value between the terminal 17 and a terminal 18 as a detected cell voltage value of the cell 35.

The terminals 13 to 18 function as monitoring terminals of the protecting IC 10 for monitoring the cell voltages of the cells 31 to 35. The terminal 13 is connected to the cell connecting terminal 41. The terminal 14 is connected to the cell connecting terminal 42. The terminal 15 is connected to the cell connecting terminal 43. The terminal 16 is connected to the cell connecting terminal 44. The terminal 17 is connected to the cell connecting terminal 45. The terminal 18 is connected to the cell connecting terminal 46. The terminal 13 is connected to the electric power line 9b. The terminal 13 is, for example, a negative power supply terminal (a VSS terminal) of the protecting IC 10. The terminal 18 is connected to the electric power line 9a. The terminal 18 is, for example, a positive power supply terminal (a VDD terminal) of the protecting IC 10.

The charge and discharge controlling unit 7 includes an overcharge detecting circuit outputting an abnormal charge detecting signal if at least one of the detected cell voltage values is a predetermined overcharge detecting threshold or greater where it is assumed that overcharge of the cells 31-35 forming the secondary battery 30 is detected. The charge and discharge controlling unit 7 outputs a low level signal for turning off the transistor 1 from the terminal 11 when the abnormal charge detecting signal for the secondary battery 30 is output. With this, the cells 31 to 35 forming the secondary battery 30 can be prevented from overcharging irrespective of turning on or off the transistor 2.

The charge and discharge controlling unit 7 includes an overdischarge detecting circuit outputting an abnormal discharge detecting signal if at least one of the detected cell voltage values is a predetermined overdischarge detecting threshold or smaller where it is assumed that overdischarge of the cell forming the secondary battery 30 is detected. The charge and discharge controlling unit 7 outputs a low level signal for turning off the transistor 2 from the terminal 12 when the abnormal discharge detecting signal for the secondary battery 30 is output. With this, the cells 31 to 35 forming the secondary battery 30 can be prevented from overdischarging irrespective of turning on or off the transistor 1.

The charge and discharge controlling unit 7 may have a charging overcurrent detecting circuit. The charging overcurrent detecting circuit detects whether a negative interterminal voltage (the voltage between the load connecting terminal 6 and the cell connecting terminal 41) is a predetermined charging overcurrent detecting threshold or smaller. If the charging overcurrent detecting circuit detects that the negative interterminal voltage is the predetermined charging overcurrent detecting threshold or smaller, the abnormal charge detecting signal is output by assuming that an overcurrent (a charging overcurrent) in a direction of charging the secondary battery 30 is detected. The charge and discharge controlling unit 7 turns off the transistor 1 by outputting a low level signal from the terminal 11 of the protecting IC 10 when the abnormal charge detecting signal is output from the charging overcurrent detecting circuit. With this, the secondary battery 30 can be protected from the charging overcurrent irrespective of turning on or off the transistor 2.

The charge and discharge controlling units 7 may have a discharging overcurrent detecting circuit. The discharging overcurrent detecting circuit detects whether the negative interterminal voltage (the voltage between the load connecting terminal 6 and the cell connecting terminal 41) is a predetermined discharging overcurrent detecting threshold or greater. If the discharging overcurrent detecting circuit detects that the negative interterminal voltage is the predetermined discharging overcurrent detecting threshold or greater, the abnormal discharge detecting signal is output by assuming that an overcurrent (a discharging overcurrent) in a direction of discharging the secondary battery 30 is detected. The charge and discharge controlling unit 7 turns off the transistor 2 by outputting a low level signal from the terminal 12 of the protecting IC 10 if the abnormal discharge detecting signal is output from the discharging overcurrent detecting circuit. With this, the secondary battery 30 can be protected from the discharging overcurrent irrespective of turning on or off the transistor 1.

Further, the charge and discharge controlling unit 7 includes a disconnection detecting circuit for outputting an abnormal disconnection detecting signal indicative of disconnection of at lease one of the terminals 14 to 17. The charge and discharge controlling unit 7 outputs a low level signal for turning off the transistor 1 from the terminal 11 and a low level signal for turning off the transistor 2 from a terminal 12 if an abnormal disconnection detecting signal is output. With this, it is possible to prevent the transistor 1 or 2 from being turned off even if a defect in the charged state of any one of the cells 31 to 35, which form the secondary battery 30, is not detected by a charge and discharge controlling unit 7 when any one of the terminals 14 to 17 is broken. As a result, it is possible to prevent the defect in the charged state of any one of the cells 31 to 35 from continuing. The defect in the charged state is, for example, a false overcharge detected by the overcharge detecting circuit, a false overdischarge detected by the overdischarge detecting circuit, or the like.

The charge and discharge controlling unit 7 may output a disconnection reporting signal for reporting detection of the disconnection to an external unit such as the outer load 90 if the abnormal disconnection detecting signal is output. The external device such as the outer load 90 may store error information indicative of the disconnection into a readable memory device or report to a user upon receipt of the disconnection reporting signal.

Figure 2:
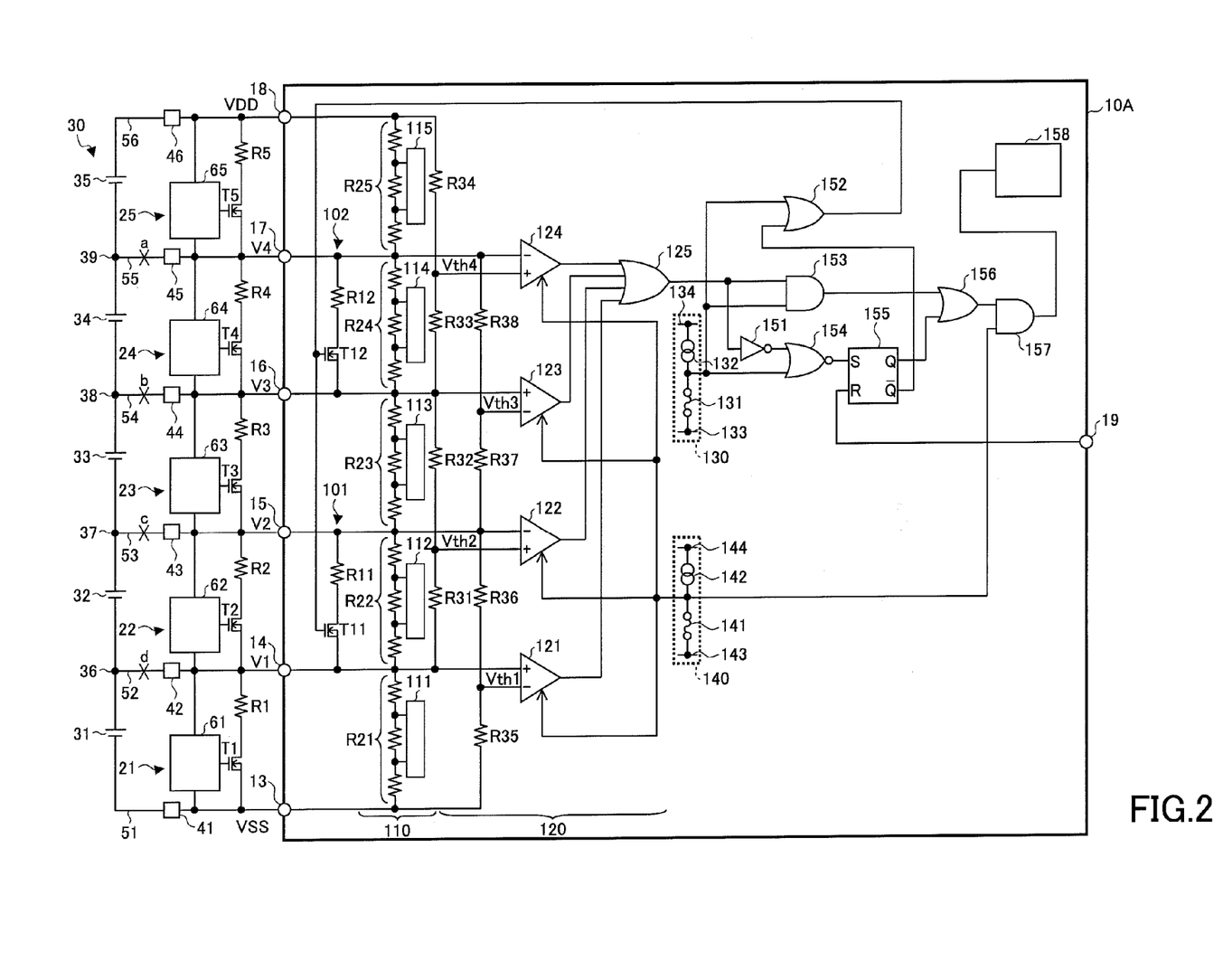
FIG. 2 illustrates an exemplary structure of a battery protecting IC.

FIG. 2 illustrates an exemplary structure of the charge and discharge controlling unit 7 and the cell balancing circuits 21 to 25.

The charge and discharge controlling unit 7 of a protecting IC 10A includes a charge abnormality detecting circuit 110, intermediate potential fixing circuits 101 and 102, a disconnection detecting circuit 120, a latching circuit 155, and a controlling circuit 158.

The charge abnormality detecting circuit 110 detects a defect in the charged state of the secondary battery 30. The charge abnormality detecting circuit 110 includes bleeder resistors R21-R25 and detectors 111-115 provided for the respective cells 31 to 35 to thereby form the overcharge detecting circuit or the overdischarge detecting circuit.

The bleeder resister R21 is connected to the cell 31 in parallel via the terminals 13 and 14. The bleeder resister R22 is connected to the cell 32 in parallel via the terminals 14 and 15. The bleeder resister R23 is connected to the cell 33 in parallel via the terminals 15 and 16. The bleeder resister R24 is connected to the cell 34 in parallel via the terminals 16 and 17. The bleeder resister R25 is connected to the cell 35 in parallel via the terminals 17 and 18. The bleeder resistors R21 to R25 have the same resistance value.

The bleeder resistance R21 detects a value obtained by dividing the voltage between the terminals 13 and 14 using a first ratio as an overcharge determining value of the cell 31. The bleeder resistance R21 detects a value obtained by dividing the voltage between the terminals 13 and 14 using a second ratio as an overdischarge determining value of the cell 31. The bleeder resistors R22 to R25 detect overcharge determining value and an overdischarge determining values corresponding to the cells 32 to 35 by detecting the voltages between the terminals using the same ratios for dividing the voltages as the first ratio and the second ratio, respectively.

If the overcharge determining value detected by the bleeder resistor R21 is the overcharge detecting threshold or greater, the detector 111 outputs an overcharge detecting signal for the cell 31. If the overdischarge determining value detected by the bleeder resistor R21 is the overcharge detecting threshold or smaller, the detector 111 outputs an overdischarge detecting signal for the cell 31. In a manner similar to the detector 111, the detectors 112 to 115 output the overcharge detecting signals and the overdischarge detecting signals based on the values detected by the bleeder resistors R22 to R25, respectively. The detectors 111 to 115 are formed by, for example, comparators.

The charge abnormality detecting circuit 110 functions as an overcharge detecting circuit which outputs the abnormal charge detecting signal to the controlling circuit 158 when the overcharge detecting signal is output from at least one of the detectors 111 to 115. The charge abnormality detecting circuit 110 functions as an overdischarge detecting circuit which outputs the abnormal discharge detecting signal to the controlling circuit 158 when the overdischarge detecting signal is output from at least one of the detectors 111 to 115. When the controlling circuit 158 receives the abnormal charge detecting signal, the transistor 1 of FIG. 1 is turned off. When the controlling circuit 158 receives the abnormal discharge detecting signal, the transistor 2 of FIG. 1 is turned off.

The intermediate potential fixing circuit 101 is inserted between the terminals 14 and 15 as illustrated in FIG. 2. The intermediate potential fixing circuit 101 is connected to the cell 32 in parallel via the terminals 14 and 15. The intermediate potential fixing circuit 101 includes an electric current pathway into which a series circuit of a resistor R11 and a transistor T11 are inserted. The transistor T11 is turned on in an initial state before a disconnection occurs between an intermediate electric potential point 36 of the secondary battery 30 and the terminal 14 or a disconnection occurs between an intermediate electric potential point 37 of the secondary battery 30 and the terminal 15.

The intermediate potential fixing circuit 101 is a shifting circuit for shifting the electric potential of the terminal 14 (the midpoint electric potential between the terminals 13 and 15) to the electric potential of the terminal 15 when the disconnection occurs between the intermediate electric potential point 36 of the secondary battery 30 and the terminal 14. The intermediate potential fixing circuit 101 is a shifting circuit for shifting the electric potential of the terminal 15 (the midpoint electric potential between the terminals 14 and 16) to the electric potential of the terminal 14 when the disconnection occurs between the intermediate electric potential point 37 of the secondary battery 30 and the terminal 15. The intermediate electric potential point 36 is a connecting point between the negative terminal of the cell 32 and the positive terminal of the cell 31. The intermediate electric potential point 37 is a connecting point between the negative terminal of the cell 33 and the positive terminal of the cell 32.

The intermediate potential fixing circuit 102 is inserted between the terminals 16 and 17. The intermediate potential fixing circuit 102 is connected to the cell 34 in parallel via the terminals 16 and 17. The intermediate potential fixing circuit 102 includes an electric current pathway into which a series circuit of a resistor R12 and a transistor T12 are inserted. The transistor T12 is turned on in the initial state before a disconnection occurs between an intermediate electric potential point 38 of the secondary battery 30 and the terminal 16 or a disconnection occurs between an intermediate electric potential point 39 of the secondary battery 30 and the terminal 17.

The intermediate potential fixing circuit 102 is a shifting circuit for shifting the electric potential of the terminal 16 (the midpoint electric potential between the terminals 15 and 17) to the electric potential of the terminal 17 when a disconnection occurs between the intermediate electric potential point 38 of the secondary battery 30 and the terminal 16. The intermediate potential fixing circuit 102 is a shifting circuit for shifting the electric potential of the terminal 17 (the midpoint electric potential between the terminals 16 and 18) to the electric potential of the terminal 16 when the disconnection occurs between the intermediate electric potential point 39 of the secondary battery 30 and the terminal 17. The intermediate electric potential point 38 is a connecting point between the negative terminal of the cell 34 and the positive terminal of the cell 33. The intermediate electric potential point 39 is a connecting point between the negative terminal of the cell 35 and the positive terminal of the cell 34.

The disconnection detecting circuit 120 includes comparators 121 to 124. The comparator 121 is a detector which detects the disconnection between the intermediate electric potential point 36 and the terminal 14 based on the electric potential of the terminal 14. The comparator 122 is a detector which detects the disconnection between the intermediate electric potential point 37 and the terminal 15 based on the electric potential of the terminal 15. The comparator 123 is a detector which detects the disconnection between the intermediate electric potential point 38 and the terminal 16 based on the electric potential of the terminal 16. The comparator 124 is a detector which detects the disconnection between the intermediate electric potential point 39 and the terminal 17 based on the electric potential of the terminal 17.

The comparator 121 outputs a disconnection detecting signal being a high level indicating that the disconnection between the intermediate electric potential point 36 and the terminal 14 is detected if the electric potential of the terminal 14 pulled up by the terminal 15 is a disconnection detecting threshold Vth1 or greater. The comparator 122 outputs a disconnection detecting signal being a high level indicating that the disconnection between the intermediate electric potential point 37 and the terminal 15 is detected if the electric potential of the terminal 15 pulled down by the terminal 14 is a disconnection detecting threshold Vth2 or smaller. The comparator 123 outputs a disconnection detecting signal being a high level indicating that the disconnection between the intermediate electric potential point 38 and the terminal 16 is detected if the electric potential of the terminal 16 pulled up by the terminal 17 is a disconnection detecting threshold Vth3 or greater. The comparator 124 outputs a disconnection detecting signal being a high level indicating that the disconnection between the intermediate electric potential point 39 and the terminal 17 is detected if the electric potential of the terminal 17 pulled down by the terminal 16 is a disconnection detecting threshold Vth4 or smaller.

The disconnection detecting threshold Vth1 is generated by a resistance voltage dividing circuit formed of resistors R35 and R36 connected in series. The resistance voltage dividing circuit is inserted between the terminals 13 and 15. The resistance voltage dividing circuit is connected to the series circuit of the cells 31 and 32 in parallel via the terminals 13 and 15. The disconnection detecting threshold Vth2 is generated by a resistance voltage dividing circuit formed of resistors R31 and R32 connected in series. The resistance voltage dividing circuit is inserted between the terminals 14 and 16. The resistance voltage dividing circuit is connected to the series circuit of the cells 32 and 33 in parallel via the terminals 14 and 16. The disconnection detecting threshold Vth3 is generated by a resistance voltage dividing circuit formed of resistors R37 and R38 connected in series. The resistance voltage dividing circuit is inserted between the terminals 15 and 17. The resistance voltage dividing circuit is connected to the series circuit of the cells 33 and 34 in parallel via the terminals 15 and 17. The disconnection detecting threshold Vth4 is generated by a resistance voltage dividing circuit formed of resistors R33 and R34 connected in series. The resistance voltage dividing circuit is inserted between the terminals 16 and 18. The resistance voltage dividing circuit is connected to the series circuit of the cells 34 and 35 in parallel via the terminals 16 and 18.

The disconnection detecting circuit 120 includes an OR circuit 125 which outputs an abnormal disconnection detecting signal being a high level if the disconnection detecting signal is output from at least one of the comparators 121 to 124. The controlling circuit 158 performs a predetermined operation when the disconnection occurs by receiving the abnormal disconnection detecting signal via the latching circuit 155. For example, the controlling circuit 158 may turn off the transistor 1 or 2 illustrated in FIG. 1 or output the disconnection reporting signal reporting that the disconnection is detected.

The latching circuit 155 is a RS flip-flop for retaining a result of detecting a disconnection in the disconnection detecting circuit 120. An output signal from the OR circuit 125 is input into a set terminal S via a NOT circuit 151 and a NOT-OR circuit 154 to a set terminal S of the latching circuit 155. When the protecting IC 10A includes the latching circuit 155, the protecting IC 10A can prevent detection of the disconnection with the disconnection detecting circuit 120 from being canceled by variation of the electric potentials of the terminals 14 to 17 after detecting the disconnection with the disconnection detecting circuit 120.

For example, if a disconnection between the intermediate electric potential point 39 and the terminal 17 is not a complete disconnection, the electric potential of the terminal 17 may unstably move up and down. A result of detecting disconnection with the comparator 124 can be retained in the latching circuit 155. Disconnections between the intermediate electric potential point 36-38 and the terminals 14 to 16 are similarly handled.

For example, when the connecting wire 55 is disconnected, the cell balancing circuit 25 is operated. Then, the electric potential of the terminal 17 may unstably move up and down relative to the disconnection detecting threshold Vth4. However, a result of detecting the disconnection obtained by the comparator 124 can be retained by the latching circuit 155.

For example, the cell balancing circuit 25 includes the cell balancing IC 65 and a series circuit between a resistor R5 and a transistor T5. The cell balancing IC 65 is an integrated circuit which drives the transistor T5 depending on the cell voltage of the cell 35 or the voltage between the terminals 17 and 18. The series circuit of the resistor R5 and the transistor T5 is inserted between the cell connecting terminals 45 and 46. The series circuit of the resistor R5 and the transistor T5 is connected to the cell 35 in parallel via the terminals 45 and 46.

If the cell voltage of the cell 35 is a predetermined threshold for starting discharging or greater, the cell balancing IC 65 causes the cell 35 to start discharging electricity by turning on the transistor T5. The threshold for starting discharging is set lower than the overcharge detecting threshold set by the charge abnormality detecting circuit 100. If the cell voltage of the cell 35 is a predetermined threshold for stopping discharging or smaller, the cell balancing IC 65 causes the cell 35 to stop discharging electricity by turning off the transistor T5. The threshold for stopping discharging is set higher than the overcharge detecting threshold set by the charge abnormality detecting circuit 100.

For example, if the connecting wire 55 is disconnected at a point a, the intermediate potential fixing circuit 102 causes the electric potential of the terminal 17 to decrease so that the electric potential of the terminal 17 approaches the electric potential of the terminal 16 in conformity with a ratio for dividing the voltage using the resistor R12, the resistor R24, and the resistor R25. Because of the decrement of the electric potential of the terminal 17, the cell voltage of the cell 35 applied between the both ends of the cell balancing IC 65 apparently becomes great. Therefore, the IC cell balancing IC 65 turns on the transistor T5 to thereby start discharging electricity from the cell 35. The discharging current (e.g., 20 mA) flowing through the resistor R5 is sufficiently greater than the electric currents (e.g., 2 µA) flowing through the resistors R12, R24, and R25. Therefore, the electric potential of the terminal 17 increases so as to approach the electric potential of the terminal 18. Because of the increment of the electric potential of the terminal 17, the cell voltage of the cell 35 applied between the both ends of the cell balancing IC 65 apparently becomes small. Therefore, the IC cell balancing IC 65 turns off the transistor T5 to thereby stop discharging the cell 35. By stopping discharging the cell 35, the electric potential of the terminal 17 decreases again due to the intermediate potential fixing circuit 102 so that the electric potential of the terminal 17 approaches the electric potential of the terminal 16.

As described, when the connecting wire 55 is disconnected at the point a, the electric potential of the terminal 17 may unstably move up and down. However, since the latching circuit 155 is provided, it is possible to prevent the cancellation of detecting the disconnection. Further, since adjacent cells connected to the disconnected line are discharged more than the other cells, it is possible to prevent a balance among the cell voltages of the cells from degrading. The intermediate potential fixing circuit 101 causes the electric potential of the terminal 15 to decrease so that the electric potential of the terminal 15 approaches the electric potential of the terminal 14 in conformity with a ratio for dividing the voltage using the resistor R11, the resistor R22, and the resistor R23.

The transistor T12 of the intermediate potential fixing circuit 102 is a switching circuit for stopping shifting the electric potential of the terminal 17 to the electric potential of the terminal 16 after the result of detecting disconnection obtained by the disconnection detecting circuit 120 is retained by the latching circuit 155. By turning off the transistor T12, the electric current flowing through the resistor R12 of the intermediate potential fixing circuit 102 is shut off. Therefore, the shift of the electric potential in the terminal 17 stops. Said differently, the electric potential of the terminal 17 pulled down by the intermediate potential fixing circuit 102 increases by turning off the transistor T12 to stopp the shift of the electric potential.

The transistor T12 is a switching circuit for stopping shifting the electric potential of the terminal 16 to the electric potential of the terminal 17 after the result of detecting disconnection obtained by the disconnection detecting circuit 120 is retained by the latching circuit 155. By turning off the transistor T12, the electric current flowing through the resistor R12 of the intermediate potential fixing circuit 102 is shut off. Therefore, the shift of the electric potential in the terminal 16 stops. Said differently, the electric potential of the terminal 16 pulled up by the intermediate potential fixing circuit 102 increases by turning off the transistor T12 to stop the shift of the electric potential.

As described, by providing the transistor T12 for restricting the electric current flowing through the intermediate potential fixing circuit 102, it is possible to prevent the electric potential of the terminal 17 or 16 from unstably moving up and down relative to the disconnection detecting thresholds Vth4 or Vth3 after the terminal 17 or 16 is disconnected. As a result, the cancellation of detecting the disconnection seldom occurs. This is similar in the transistor T11 of the intermediate potential fixing circuit 101.

Further, the transistor T12 of the intermediate potential fixing circuit 102 makes an input impedance between the terminals 18 and 17 and an input impedance between the terminals 17 and 16 equal after the latching circuit 155 retains the result of detecting disconnection which is obtained by the disconnection detecting circuit 120. Said differently, the transistor T12 stops the shift of the electric potential of the terminals so that the input impedance between the terminals 18 and 17 becomes the same as the input impedance between the terminals 17 and 16. For example, because the resistance values of the resistors R24 and R25 are the same, by turning off the transistor T12, the input impedance between the terminals 18 and 17 is the same as the input impedance between the terminals 17 and 16. Thus, even if the connection wire 55 is disconnected at the point a, the ratio between the input impedance between the terminals 18 and 17 and the input impedance between the terminals 17 and 16 is 1:1. Therefore, a voltage balance inside the protecting IC 10A is maintained. Thus, the action of the cell balancing IC 65 is prevented. Further, it is possible to prevent the transistor T5 from turning on or off by the action of the cell balancing IC 65. This is similar in the transistor T11 of the intermediate potential fixing circuit 101.

The transistors T11 and T12 are turned on and off in response to an output signal from an inverted output terminal (Q having an overbar) of the latching circuit 155. An output signal from the inverted output terminal (Q having the overbar) of the latching circuit 155 is input into gates of the transistors T11 and T12. An output signal from an output terminal Q of the latching circuit 155 is input into an OR circuit 156. An output signal from an AND circuit 153 is input into the OR circuit 156. Output signals from the OR circuit 125 and a latching function selecting circuit 130 are input into the AND circuit 153. The output signal from the latching function selecting circuit 130 is input into an OR circuit 152, the AND circuit 153, and the NOT-OR circuit 154.

The latching function selecting circuit 130 is a switching means for switching validity or invalidity of the latching circuit 155. The latching function selecting circuit 130 outputs a low level which is the electric potential of a low electric potential 133 when a fuse 131 is connected. With this, the function of the latching circuit 155 becomes valid. The latching function selecting circuit 130 outputs a high level which is the electric potential of a high electric potential 134 when the fuse 131 is not connected. With this, the function of the latching circuit 155 becomes invalid.

An output signal from an output terminal Q of the latching circuit 155 is input into an AND circuit 157. An output signal from a disconnection detecting function selecting circuit 140 is input into the AND circuit 157. An output signal from the AND circuit 157 is input into the controlling circuit 158.

The disconnection detecting function selecting circuit 140 is a switching means for switching over validity or invalidity of the disconnection detecting circuit 120. The disconnection detecting function selecting circuit 140 outputs a low level which is the electric potential of a low electric potential unit 143 when a fuse 141 is connected. With this, the function of the disconnection detecting circuit 120 becomes valid. The disconnection detecting function selecting circuit 140 outputs a high level which is the electric potential of a high electric potential unit 144 when the fuse 141 is not connected. With this, the function of the disconnection detecting circuit 120 becomes invalid.

Depending on whether the fuses 131 and/or 141 is cut by laser trimming, the validity or invalidity of functions of the latching circuit 155 and/or the disconnection detecting circuit 120 can be selected. With this, it is possible to easily provide the functions corresponding to each of the users using the protection IC 10A without modifying a wiring layer. Said differently, the number of man-hours in manufacturing a mask by function deployment can be reduced. Further, for example, pre-production cost, management cost, a lead time for manufacturing ICs, an evaluation time, or the like can be freed.

Further, the protecting IC 10A may have a reset terminal 19 for resetting the latching circuit 155. A reset signal input from the reset terminal 19 is input into a reset terminal R of the latching circuit 155. With this, a device provided outside the protecting circuit 10A can cancel holding of the result of detecting disconnection by the latching circuit 155 at an arbitrary timing.

For example, referring to FIG. 2, the intermediate potential fixing circuits 101 and 102 are connected in parallel to the cells on the even-numbered stages. However, the intermediate potential fixing circuit 103, 104 and 105 are connected in parallel to the cells on the odd-numbered stages as illustrated in FIG. 3. Referring to FIG. 3, positions of inverting input terminals and noninverting input terminals of comparators 121 to 124 are reversed relative to the positions of input terminals and noninverting input terminals in FIG. 2.

Figure 3:
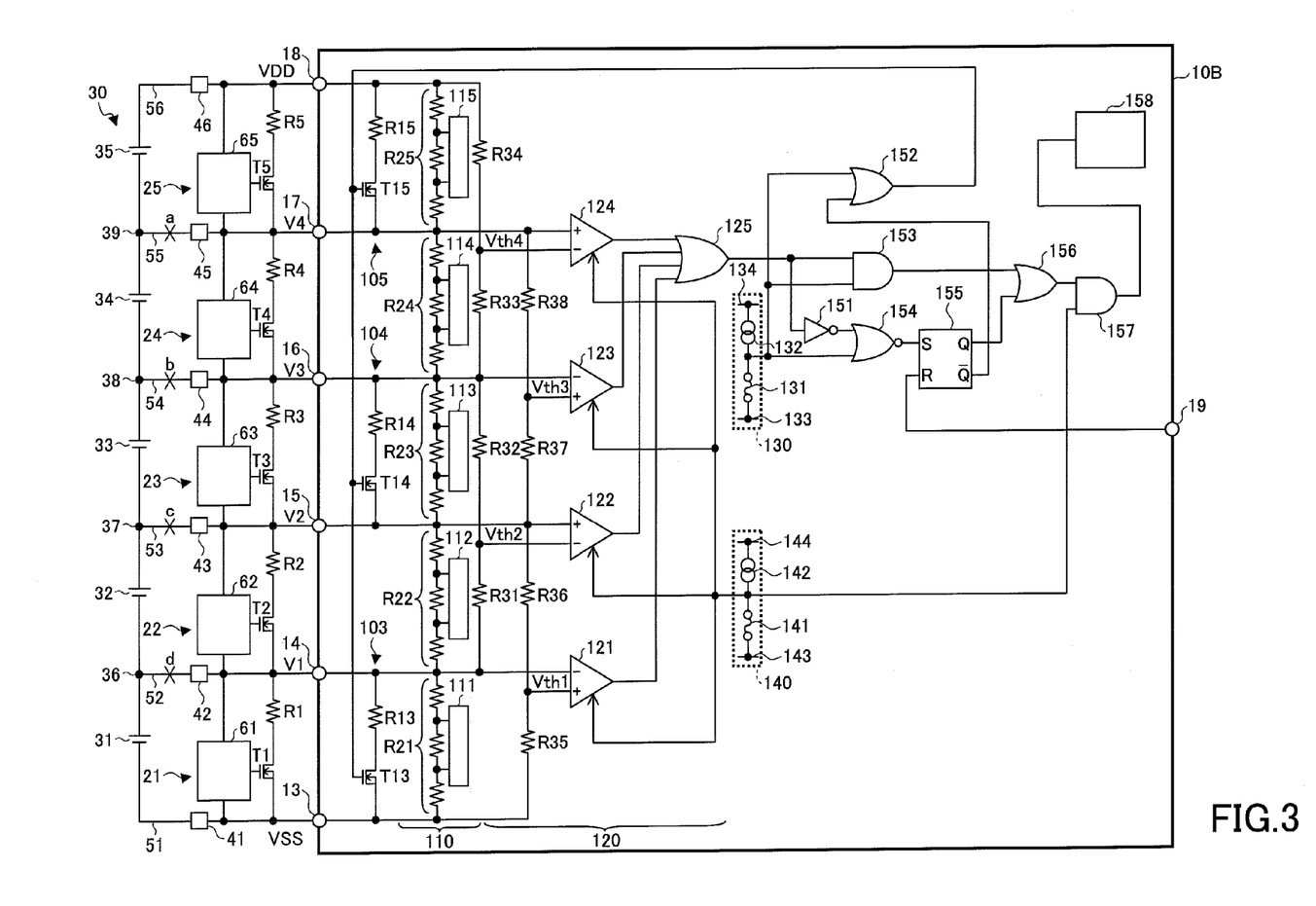
FIG. 3 illustrates an exemplary structure of a battery protecting IC.

Referring to FIG. 3, a comparator 121 outputs a disconnection detecting signal being a high level indicating that a disconnection between an intermediate electric potential point 36 and a terminal 14 is detected if the electric potential of the terminal 14 pulled down by a terminal 13 is a disconnection detecting threshold Vth1 or smaller. A comparator 122 outputs a disconnection detecting signal being a high level indicating that a disconnection between an intermediate electric potential point 37 and an terminal 15 is detected if the electric potential of the terminal 15 pulled up by a terminal 16 is a disconnection detecting threshold Vth2 or greater. A comparator 123 outputs a disconnection detecting signal being a high level indicating that a disconnection between the intermediate electric potential point 38 and the terminal 16 is detected if the electric potential of the terminal 16 pulled down by the terminal 15 is a disconnection detecting threshold Vth3 or smaller. A comparator 124 outputs a disconnection detecting signal being a high level indicating that a disconnection between an intermediate electric potential point 39 and a terminal 17 is detected if the electric potential of the terminal 17 pulled up by a terminal 18 is a disconnection detecting threshold Vth4 or greater.

For example, in the above embodiment, the number of the assembled batteries, which form the secondary battery 30 and are arranged in series, is five. However, even if the number of the assembled batteries is other than five, the embodiment is similarly applicable. Further, the positions of the transistors 1 and 2 can be mutually substituted (changed in their positions).

Within the above embodiment, the charge controlling transistor 1 and the discharge controlling transistor 2 are inserted into the electric power line 9b on the negative terminal side. However, the charge controlling transistor 1 and the discharge controlling transistor 2 may be inserted into the electric power line 9a on the positive terminal side.

Further, the above cell balancing circuits 21 to 25 are provided outside the battery protecting IC. However, the cell balancing circuits 21 to 25 may be built inside the cell balancing circuits 21 to 25.

According to the embodiment, it is possible to prevent a false operation from occurring when the disconnection is detected.

All examples and conditional language recited herein are intended for pedagogical purposes to aid the reader in understanding the embodiments and the concepts contributed by the inventor to furthering the art, and are to be construed as being without limitation to such specifically recited examples and conditions, nor does the organization of such examples in the specification relate to a showing of superiority or inferiority of the embodiments. Although the battery protecting circuit has been described in detail, it should be understood that various changes, substitutions, and alterations could be made hereto without departing from the spirit and scope of the invention.

What is claimed is:

1. A battery protecting circuit for protecting a secondary battery including at least a first cell and a second cell, which are connected in series, the battery protecting circuit comprising:
   a first terminal connected on a high potential side of the first cell;
   a second terminal connected on a low potential side of the first cell and a high potential side of the second cell;
   a third terminal connected on a low potential side of the second cell;
   a charge abnormality detecting circuit which detects abnormality of the charged state of the secondary battery;
   a shifting circuit for shifting electric potential of the second terminal on a side of the first terminal or on a side of a third terminal when a disconnection occurs between the secondary battery and the second terminal, the shifting circuit including a switching circuit;
   a disconnection detecting circuit for detecting the disconnection based on the electric potential of the second terminal; and
   a latching circuit for retaining a result detected by the disconnection detecting circuit,
   wherein, after the result detected by the disconnection detecting circuit is retained by the latching circuit, an electric potential of the second terminal is prevented from shifting by the switching circuit included in the shifting circuit.

2. The battery protecting circuit according to claim 1, wherein, after the result detected by the disconnection detecting circuit is retained by the latching circuit, the switching circuit of the shifting circuit equalizes an input impedance between the first terminal and the second terminal to an input impedance between the second terminal and the third terminal so that the electric potential of the second terminal is prevented from shifting by the switching circuit.

3. The battery protecting circuit according to claim 1, further comprising:
   a reset terminal for resetting the latching circuit.

4. The battery protecting circuit according to claim 1, further comprising:
   a switching unit for switching over validity or invalidity of the latching circuit and the disconnection detecting circuit.

5. The battery protecting circuit according to claim 4, wherein the switching unit switches over the validity or the invalidity of the latching circuit and the disconnection detecting circuit by a fuse.

6. The battery protecting circuit according to claim 1, further comprising:
   a first discharging cell for discharging the first cell if the cell voltage of the first cell is a predetermined value or greater; and
   a second discharging cell for discharging the second cell if the cell voltage of the second cell is a predetermined value or greater.

7. A battery protecting device comprising:
   the battery protecting circuit according to claim 1; and
   a shutoff unit for shutting off an electric current flowing through the secondary battery based on the result detected by the disconnection detecting circuit.

8. A battery pack comprising:
   the battery protecting device according to claim 7; and
   the secondary battery.

* * * * *